United States Patent [19]

Su et al.

[11] 4,329,335

[45] May 11, 1982

[54] AMPHOTERIC-NONIONIC BASED ANTIMICROBIAL SHAMPOO

[75] Inventors: Dean T. Su, North Brunswick; Warren R. Schubert, Somerset, both of N.J.

[73] Assignee: Colgate-Palmolive Company, New York, N.Y.

[21] Appl. No.: 205,536

[22] Filed: Nov. 10, 1980

[51] Int. Cl.³ .................. A61K 7/06; A61K 7/09; A61K 31/415
[52] U.S. Cl. .......................... 424/70; 424/71; 424/273 R; 424/DIG. 4; 252/106; 252/DIG. 13
[58] Field of Search ......... 424/70, 71, 273 R, DIG. 4; 252/DIG. 13

[56] References Cited

U.S. PATENT DOCUMENTS

| | | | |
|---|---|---|---|
| 3,658,985 | 4/1972 | Olson et al. | 424/70 |
| 3,769,398 | 10/1973 | Hewitt | 424/70 |
| 3,812,142 | 5/1974 | Meiser et al. | 424/269 |
| 3,903,287 | 9/1975 | Meiser et al. | 424/273 |
| 3,996,146 | 12/1976 | Tarasov et al. | 424/70 |
| 4,013,787 | 3/1977 | Varlerberghe et al. | 424/70 |
| 4,154,706 | 5/1979 | Kenkare et al. | 252/DIG. 13 |

FOREIGN PATENT DOCUMENTS 1502144  2/1978  United Kingdom .

Primary Examiner—Donald B. Moyer
Attorney, Agent, or Firm—Richard N. Miller; Murray M. Grill; Herbert S. Sylvester

[57]   ABSTRACT

A homogeneous liquid amphoteric-nonionic based antidandruff conditioning shampoo which includes about 0.5 to 2.5% of the antimicrobial agent, 1-imidazolyl-1-(4-chlorophenoxy)-3,3-dimethylbutan-2-one, solubilized in an aqueous solution of critical amounts of a four component mixture of the following specific ingredients:

a. about 6-30% by weight of cocobetaine, cocosulfobetaine, cocoamidobetaine, cocoamidosulfobetaine or combinations thereof,
b. about 1-7.5% by weight of a tertiary amine oxide,
c. about 1-7% by weight of a fatty acid mono- or di-ethanolamide,
d. about 0.1-5.0% by weight of a polyoxyethylene hexitan mono-higher fatty acid ester, and preferably
e. about 0.01-0.1% by weight of a polymerized quaternized ammonium compound. This shampoo is transparent in appearance and should preferably contain 65-80% water.

9 Claims, No Drawings

AMPHOTERIC-NONIONIC BASED ANTIMICROBIAL SHAMPOO

This invention relates to an amphoteric-nonionic based antidandruff shampoo containing the water-insoluble antidandruff agent, 1-imidazolyl-1-(4-chlorophenoxy)-3,3-dimethylbutan-2-one, solubilized in an aqueous solution of critical amounts of specific amphoteric and nonionic components, capable of both cleansing and conditioning the hair in a single operation, by simply washing the hair therewith.

PRIOR ART

The prior art antidandruff shampoos contain organozinc compounds such as zinc pyrithione, which is not soluble in a liquid shampoo, resulting in a non-homogeneous, milky shampoo wherein the insoluble antidandruff agent may be unevenly dispersed in and/or precipitates out of the shampoo composition.

The imidazolyl ketones such as 1-imidazolyl-1-(4 chlorophenoxy)-3,3-dimethylbutan-2-one, are disclosed in U.S. Pat. Nos. 3,812,142 and 3,903,287 as antimycotic agents, useful in pharmaceutical compositions including aqueous suspensions containing surface active agents such as polyoxyethylene sorbite and sorbitane esters. British Pat. No. 1,502,144 and its German counterpart, Pat. No. 2,430,039, disclose cosmetic compositions such as shampoos containing the imidazolyl ketone antimycotic agents dispersed in a dermatologically acceptable carrier which contains a detergent-active compound. The shampoos are in the form of creams, aerosols, powders and liquids. Although nonionic, amphoteric and cationic surfactants are listed, the specific liquid shampoos disclosed contain 50% anionic surfactant and 3.5-5% of the nonionic fatty acid diethanolamide. German Pat. No. 2,600,800 discloses the 1-imidazolyl-1-(4-chlorophenoxy)-3,3-dimethylbutan-2-one in a fungicidal composition, which may be in the form of a dispersion in water, as useful for protecting plaster coatings, dispersion dyes, wall-paper, tiled surfaces, paints, glues, bitumina, furniture, leather, shower curtains, textiles, carpets, wood and paper. German Pat. No. 2,700,806 also discloses a mixture of the imidazolyl ketone fungicide and a quaternary ammonium bactericide useful for protecting materials such as paints, glues, bitumen, cellulose, paper, textiles, leather and wood.

Although the prior art discloses the specified imidazolyl ketone as an antimycotic agent, and its use in various formulations including shampoos, said liquid compositions are usually in the form of suspensions and/or dispersions. When in suspension form, this is due to the water-insolubility property of the imidazolyl ketones, and results in opaque and milky non-homogeneous liquid shampoos, similarly to the organozinc-containing shampoos.

In addition to the antidandruff agent, shampoos must include surfactants, usually based on anionic detergents, as shown in aforedescribed British Pat. No. 1,502,144. However, nonionic and/or amphoteric detergents may be substituted for all or part of said anionic detergents as shown by U.S. Pat. No. 4,009,256, wherein the aqueous shampoo composition comprises 1-25% amphoteric agent such as the imidazoline derivatives or the amido betaines, plus 0-20% of either a nonionic surfactant such as the amine oxides or an anionic surfactant. Similarly, U.S. Pat. No. 3,658,985 discloses an oil and fluorescent dye containing liquid shampoo comprising a detergent mixture of 1-18% higher alkyl amine oxide, 2-20% amphoteric surfactant such as betaine or sultaine and 0.5-10% of a quaternary ammonium salt, in lieu of the preferred anionic detergent. U.S. Pat. No. 3,769,398 also discloses a liquid shampoo containing a detergent selected from the group consisting of betaines, sulfobetaines, amine oxides and mixtures thereof, free of anionic-acting surfactants and containing a water soluble polyethyleneimine polymer as an antimicrobial agent. An all nonionic liquid shampoo free of ionic materials is also disclosed in U.S. Pat. No. 4,154,706, containing three nonionic components: an amine oxide, a polyethoxylated hexitan ester and either a higher alkoxy polyoxyethylene ethanol or an alkyl glycoside or a mixture thereof, or a 5-6 component composition, wherein a polyacrylamide and an alkanolamide may be added to the three component system or substituted for the polyoxyethylene ethanol or alkyl glycoside component. U.S. Pat. No. 4,013,787 further discloses a film forming cationic polymer conditioning agent in cosmetic hair compositions including nonionic based or amphoteric based or cationic based or anionic based liquid shampoos. U.S. Pat. No. 3,996,146 further discloses an acid pH clear shampoo comprising 0.05-2.5% of a quaternary ammonium polymer conditioning agent in a multidetergent system containing 10-25% of at least two anionic detergents and 4-15% of an amphoteric surfactant such as betaine.

However, there is no disclosure of the imidazolyl ketone antimicrobial agent solubilized in an amphoteric-nonionic based aqueous conditioning shampoo.

DESCRIPTION OF THE INVENTION

It has now been found that a mixture of specified nonionic and amphoteric components in critical amounts solubilizes the insoluble imidazolyl ketone in an aqueous solution in the production of a homogeneous liquid antimicrobial conditioning shampoo.

Accordingly, it is an object of present invention to provide a homogeneous liquid antimicrobial shampoo.

Another object of this invention is to provide a liquid shampoo capable of both cleansing and conditioning the hair in a single operation.

Still another object of this invention is to provide an aqueous liquid shampoo containing 1-imidazolyl-1-(4-chlorophenoxy)-3,3-dimethylbutan-2-one solubilized in said aqueous medium.

Another object of this invention is to provide an amphoteric and nonionic based shampoo capable of solubilizing aforesaid imidazolyl ketone agent in the production of a clear homogeneous liquid shampoo.

Other objects of this invention will become apparent to those skilled in the art upon reading the following specification.

Accordingly, the present invention relates to a homogeneous liquid amphoteric-nonionic based conditioning shampoo containing an effective amount of 1-imidazolyl-1-(4-chlorophenoxy)-3,3-dimethylbutan-2-one solubilized in an aqueous vehicle containing an amphoteric surfactant selected from the group consisting of betaines, sulfobetaines, amidobetaines, amidosulfobetaines and mixtures thereof; a polyoxyethylene hexitan mono-higher fatty acid ester; a tertiary amine oxide; a fatty acid mono- or di-ethanolamide; and preferably a polymerized quaternized ammonium compound as the essential components in certain specified amounts.

The antimicrobial agent utilized in instant invention is 1-imidazolyl-1-(4-chlorophenoxy)-3,3-dimethylbutan-2-one having the structural formula:

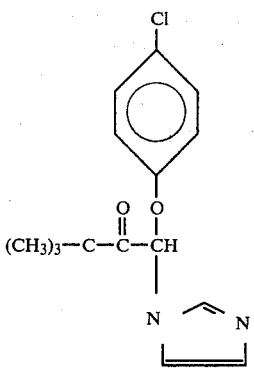

which is prepared by reacting 1-bromo-1-(4-chlorophenoxy)-3,3-dimethylbutan-2-one with imidazole dissolved in acetonitrile as disclosed in U.S. Pat. Nos. 3,812,142 and 3,903,287, which is made a part of this specification. This imidazolyl ketone is a water insoluble crystalline powder having a melting point of 94.5°–97.8° C. which may be obtained from the Bayer Company.

Solubility studies using 2 g. of the imidazolyl ketone agent plus 5 g. polyoxyethylene (20) sorbitan mono-laurate (Tween 20) or 5 g. lauric myristic diethanolamide (LMDEA) or mixtures of 4, 3, 2, 1 g. Tween 20 and 1, 2, 3, 4 g. LMDEA respectively in 93 g. of water, wherein the resultant liquid was cloudy and the ingredients separated out. Similarly, poor solubility results were obtained by combining 3.5 g. of a solution of 100 g. imidazolyl ketone agent in 250 g. LMDEA with 16.7 g. myristyl dimethylamine oxide (30% active) (MO) in 79.8 g. water, or with 8.4 g. MO in 88.1 g. water, or with 3.3 g. MO in 9.2. g. water, wherein the resultant products were cloudy with fine precipitates. On the other hand, when 3.5 g. of the aforedefined imidazolyl solution in LMDEA was mixed with 33.3 g. MO in 63.2 g water, a clear solution was obtained. This 33.3 g. MO represents a 10% active content, whereas the cloudy products represent 5%, 2.5% and 1% active concentrations respectively. Thus, it is apparent that the amounts and specificity of ingredients are critical in order to solubilize the antimicrobial imidazolyl compound in an aqueous medium in order to obtain a clear shampoo. It has further been found that the imidazolyl compound must first be solubilized in a nonionic medium prior to the addition of ionic materials thereto.

It has additionally been found that this antimicrobial agent is nonionic as a result of steric hindrance effects. The effective concentration of this agent useful in the present aqueous shampoo vehicle is preferably about 0.5–2.5% by weight of the total shampoo.

Accordingly, the shampoo vehicle constitutes about 65–80% water containing critical amounts of specifically essential nonionic and amphoteric compounds to effect an aqueous vehicle for dissolution of the aforesaid antimicrobial agent.

The essential nonionic and amphoteric components contained in this shampoo comprise an amphoteric surfactant such as the betaine or sulfobetaine or amidobetaine or amidosulfobetaine wherein said betaine contains a higher alkyl group of 10 to 20 carbon atoms, a polyethoxylated hexitan ester, a tertiary amine oxide, and a higher fatty acid ethanolamide and preferably a polymerized quaternized ammonium compound, in certain critical amounts in order to avoid precipitation of the antimicrobial agent.

More specifically, the instant shampoo is based on four essential components comprising about 6–30% and preferably 7.5–15% by weight of an amphoteric agent selected from the group consisting of betaine, sulfobetaine, amidobetaine, amidosulfobetaine and mixtures thereof, about 0.1–5% and preferably about 1–2.5% by weight of a polyoxyethylene hexitan mono-higher fatty acid ester having about 20 moles of ethylene oxide per mol, about 1–7.5% and preferably 3–5% by weight of dimethyl higher alkyl tertiary amine oxide, and about 1–7% by weight of a higher fatty acid mono- or di-ethanolamide, and preferably a fifth ingredient, about 0.01–0.1% by weight of a water soluble polymerized quaternized ammonium compound.

The amphoteric surfactant component of instant liquid shampoo formulation provides both cleansing and conditioning action to the composition and is selected from the group consisting of betaines, sulfobetaines, amidobetaines, amidosulfobetaines and mixtures thereof, having the following general formula:

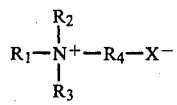

wherein $R_1$ is an alkyl group having 10 to about 20 carbon atoms, preferably 12 to 16 carbon atoms or the amido radical:

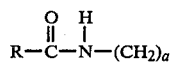

wherein R is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and optionally, one hydroxyl group and X is an anion selected from the group consisting of $SO_3=$ and $COO=$. Typical alkyldimethyl betaines include decyldimethyl betaine or 2-(N-decyl-N,N-dimethyl ammonio) acetate, cocodimethyl betaine or 2-(N-coco-N,N-dimethyl-ammonio) acetate, myristyl dimethyl betaine, palmityl dimethyl betaine, lauryl dimethyl betaine, cetyl dimethyl betaine, stearyl dimethyl betaine, etc. Typical sulfobetaines or sultaines similarly include coco dimethyl sulfobetaine or 3-(N-coco-N,N-dimethyl-ammonio) propane-1-sulfonate, myristyl dimethyl sulfobetaine, palmityl dimethyl sulfobetaine, lauryl dimethyl sulfobetaine, etc. The amidobetaines and amidosulfobetaines similarly include cocoamido ethylbetaine, cocoamidoethylsulfobetaine, and the like.

The polyoxyethylene hexitan mono-higher fatty acid ester component of present liquid shampoo provides cleaning action and functions as a dispersant. The useful compounds in this group include esters having from 10–20 carbon atoms in the higher fatty acyl thereof and 4–100, preferably 10–80 mols of ethylene oxide per mol. Preferably, the hexitan is sorbitan, although mannitan and other hexitans are also often useful, the higher fatty acyl will be of 10–16 or 20 carbon atoms, more preferably of 12–16 or 18 carbon atoms and most preferably of about 12 carbon atoms, and the number of ethoxies will be from 15–80, often preferably about 20. Especially useful in an I.C.I. product sold under the trade name Tween 20, also known as Polysorbate 20 which is polyoxyethylene (20) sorbitan monolaurate. Similarly useful products are sold under similar identifications, such as Tweens 40, 60 65 and 80, all of which are nonionic surface active agents wherein the higher fatty acyl is palmitoyl, stearoyl or oleyoyl and the number of the mols of ethylene oxide per mol is about 20. However, of these materials the polyoxyethylene sorbitan monolaurate is susually favored. Polyoxyethylene (80) sorbitan monolaurate may be used in place of said polysorbate 20.

The amine oxide component of instant liquid shampoo provides both cleaning and conditioning properties to the shampoo, and is nonionic in the pH range of the shampoo, which is normally within the range of 6.5 to 7.5 and preferably 6.8 to 7.3 or about 7. The amine oxides useful herein have the structural formula:

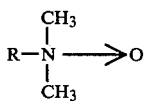

wherein R is an alkyl radical of 10–16 carbons. Examples of suitable amine oxides include dimethyl laurylamine oxide, dimethylacetyl amine oxide and dimethyl myristyl amine oxide. Of course, as with the other components of the present composition, the amine oxides will usually be chosen for desired solubility in the aqueous medium employed and for compatibility with the other components of the shampoo.

The ethanolamine component of instant liquid shampoo functions primarily as a foam booster. Useful compounds in this group include mono- and di-ethanolamides of higher fatty acides having about 10–18 carbon atoms in the acyl group. Specific examples of suitable ethanolamides include cocomonoethanolamide, cocodiethanolamide, lauric myristic diethanolamide, lauric monoethanolamide, or combinations thereof.

The polymerized quaternized ammonium compound, which is an optional but a preferably additional ingredient in the instant clear liquid shampoo, provides excellent conditioning properties to the composition, and may be defined as a polymer having a molecular chain containing unit of the formula:

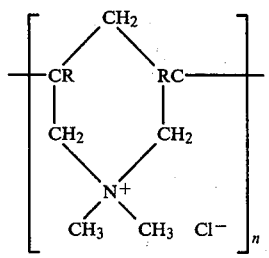

wherein R is a hydrogen or methyl and n is an integer in the range of 500 to 1000. These quaternary polymers derived from dimethyl diallyl ammonium salts are cationic, water soluble, have an average molecular weight between 75,000 and 500,000 and retain their cationic activity in the shampoo composition. A particularly suitable homopolymer of this type having a molecular weight less than 100,000 is marketed commercially as a 40% aqueous solution under the tradename MERQUAT 100, by Merck and Co., Inc. Rahway, N.J.

All of the aforesaid components in this shampoo are water-soluble and remain water-soluble during storage of the shampoo.

This particular combination of betaine, hexitan monoester, amine oxide and fatty acid ethanolamide, with or without the quaternary polymer, provides a balanced, amphoteric and nonionic surface active system which solubilized the antimicrobial agent and has desirable foaming, lathering, detersive and conditioning properties, as well as desirable viscosity characteristics. This homogeneous liquid shampoo is capable of both washing and conditioning the hair in a single operation by simply shampooing. An additional and essential function of the instant amphoteric nonionic-based shampoo is the concommitant antimicrobial action afforded by the specific imidazolyl ketone.

In addition to the previously mentioned constituents of the liquid shampoo one may also employ normal and conventional adjuvants, provided they do not adversely affect the properties of the shampoo. Thus, there may be used various coloring agents and perfumes; ultraviolet light absorbers such as the Uvinuls, which are products of GAF Corporation, preservatives such as formaldehyde or hydrogen peroxide; pearlescing agents and opacifiers; solvents, such as ethanol, preferably in the form of a specially denatured alocohol, and glycols (ethylene glycol is useful as a clarifying agent, to prevent high and low temperature clouding of desirably clear shampoos); lubricants, such as mineral oil and higher fatty alocohols, e.g. cetyl alcohol, stearyl alcohol; quaternary antibacterial materials such as Arquad B-100 (Dimethylalkylbenzylammonium chloride); viscosity modifiers such as polyethylene glycol distearate of a molecular weight in the range of 2000–8000, sodium chloride, etc. The proportion of such adjuvant materials, in total, will normally not exceed 5% of the shampoo, and preferably less than 2% thereof. The percentage of most of such individual components will be less than 2% and preferably less than 1%.

The present shampoos are readily made by simple mixing methods from readily available components, which, on storage, do not adversely affect the entire composition. However, it is essential that the imidazolyl compound be first mixed with the nonionic components such as the ethanolamide and/or the polyoxyethylene hexitan fatty acid ester prior to the addition of the amphoteric surfactant. Thus, the products are capable of being made in desired clear form or in opaque or opalescent form. The viscosities are adjustable by changing the total percentage of active ingredients and by modifying the percentage of thickening agent, NaCL and other adjuvants. In all such cases the product made will be pourable from a relatively narrow mouth bottle (1.5 cm. diameter) and the shampoo will not be so thin as to run off the hair or hands. The viscosity of the shampoo will normally be about that of glycerin at room temperature, e.g., about 1,000 centipoises, but the viscosity may be in the broader ranges of 250–2,000 and 50–5,000 centipoises. Its viscosity may approximate those of commercially acceptable shampooes now on the market. Instead of measuring viscosity directly, as by a viscosimeter, one may employ standard laboratory flow tests, in which flow times through a restriction or tube length under a reproducible head as measured in seconds, utilizing a Raymond tube. Viscosities may preferably range from 10–80 seconds and up to 300 or 400 seconds. The shampoo viscosity and the shampoo itself remain stable on storage for lengthy periods of time, without color changes or settling out of any insoluble materials.

These products have unexpectedly desirable properties. For example, the foam quality and lubricity is comparable to standard shampoos based on triethanolamine lauryl sulfate. Further, such shampoos clean the hair exceptionally well and leave it easy to comb, manageable and of low raspiness, are less drying, leaving the hair with a softer feel, producing fewer split ends after shampooing, and being easier to comb and causing less flyaway effect.

The following examples illustrate but do not limit the invention. Unless otherwise mentioned, all percentages in the examples and elsewhere in the specification are by weight and all temperatures are in °C.

CLEAR ANTIMICROBIAL SHAMPOOS

EXAMPLE 1

| | % |
|---|---|
| 12C LONZAINE/(coco dimethyl betaine) | 7.5 |
| Ammonyx MO (myristyl dimethyl amine oxide) | 7.5 |
| LMDEA (lauric myristic diethanolamide) | 5.0 |
| Polysorbate 20 (polyoxethylene (20) sorbitan monolaurate) | 2.5 |
| Climbazole (Bayer Co.) (1-imidazolyl-1-(4-chlorophenoxy)-3,3-dimethylbutan-2-one) | 2.0 |
| Formaldehyde | 0.2 |
| Water | 75.3 |

The Climbazole, LMDEA and the Polysorbate 20 are mixed together until homogeneous and clear. 25% by weight of a 30% aqueous solution of Ammonyx MO is added with stirring. 22.05% by weight of a 35% aqueous solution of Lonzaine 12C is subsequently added with agitation, followed by the addition of the water and formaldehyde. The mixture is agitated for one hour. This product is a clear solution with no sign of particulate suspension or precipitation. It is very important to first dissolve the Climbazole in LMDEA and Polysorbate 20 to give a clear and viscous solution.

The resultant product is an excellent conditioning shampoo of desired viscosity, foaming power, foam stability, antimicrobial activity and good shampooing effects, i.e., leaves the wet hair easy to comb, with a soft feel and static free.

In the shampooing described herein and in subsequent examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE 2

| | % |
|---|---|
| Lonzaine CS (Cocoamidopropylsultaine*) | 12.0 |
| Ammonyx MO | 3.0 |
| LMDEA | 5.0 |
| Polysorbate 20 | 2.0 |
| Merquat 100 (quaternary polymer - m.w. less than 100,000) | 1.0 |
| Climbazole | 2.0 |
| Formaldehyde | 0.2 |
| Water | 74.8 |

*N-cocoamidopropyl-N,N-dimethyl-N-2-hydroxypropyl-1-sulfonate

The Climbazole, LMDEA and the Polysorbate are mixed well until no particulate material is evident. 34.30% by weight of a 35% aqueous Lonzaine CS solution is added with stirring, followed by the addition of 10% by weight of a 30% aqueous Ammonyx MO solution while continuously mixing 2.5% by weight of a 40% aqueous Merguat 100 solution is added followed by the water and formaldehyde with stirring. This product is a clear solution with no sign of particulate suspension or precipitation.

EXAMPLE 3

| | % |
|---|---|
| Lonzaine CS | 12.0 |
| Ammonyx MO | 3.0 |
| Polysorbate 20 | 5.0 |
| LMDEA | 2.5 |
| Merquat 100 | 1.0 |
| Climbazole | 2.0 |
| Formaldehyde | 0.2 |
| Water | 74.3 |

This product is prepared in accordance with the procedure of Example 2.

EXAMPLE 4

| | % |
|---|---|
| Lonzaine C (Cocoamidopropylbetaine) | 12.0 |
| Ammonyx MO | 4.5 |
| Merquat 100 | 0.1 |
| Polysorbate 20 | 3.0 |
| LMDEA | 2.0 |
| Climbazole | 2.0 |
| Perfume | 1.0 |
| Deionized Water | 75.4 |

This shampoo is prepared in accordance with the process of Example 2. The resultant product is a clear liquid shampoo with a viscosity of 75 seconds.

The products of Examples 2–4 possess similarly good antimicrobial, cleansing and conditioning properties.

EXAMPLE 5

| | % |
|---|---|
| Lonzaine C | 15.0 |
| Monamid 150 (cocomonoethanolamide) | 5.0 |
| Ammonyx MO | 3.0 |
| Climabazole | 2.0 |
| Polysorbate 20 (polyoxyethylene(20) sorbitan monolaurate) | 1.0 |
| Sodium chloride | 1.0 |
| Deionized Water | 73.0 |

This shampoo is prepared according to the process of Example 1. This formulation has good conditioning and good foaming properties and a viscosity of 407 seconds according to No. 5 Raymond tube. The viscosity may be reduced by removing the sodium choloride and reducing the amount of the amide.

EXAMPLE 6

|  | % |
| --- | --- |
| Lonzaine C | 15.0 |
| Monamid 150 | 5.0 |
| Ammonyx MO | 3.0 |
| Climbazole | 2.0 |
| Tween 20 | 1.0 |
| Sodium chloride | 1.0 |
| Arquad B-100 *(a quaternary antimicrobial agent) | 0.25 |
| Deionized Water (D. I. water) | 72.75 |

*Alkyl dimethyl benzyl ammunium chloride wherein the alkyl group is 5%-$C_{12}$, 60% C14, 30% C16 and 5% C18.

This shampoo is prepared according to the process of Example 2. This product has a viscosity of 295.8 seconds according to No. 5 Raymond tube.

EXAMPLE 7

Example 6 is repeated except that the content of Arquad B-100 is increased to 0.5% and the water content is decreased to 72.50%.

EXAMPLE 8

Example 6 is repeated except that the Arquad B-100 content is increased to 1.0% and the water content is decreased to 72%.

EXAMPLE 9

Example 6 is repeated but the Arquad B-100 content is increased to 1.5% and the water content is reduced to 71.5%

EXAMPLE 10

Example 7 is repeated but the Lonzaine C, a cocomidopropyl betaine, is replaced by Lonzaine 12 C, a cocobetaine. The viscosity of the liquid is reduced drastically.

EXAMPLE 11

Example 10 is repeated but the Arquad B-100 content is increased to 1.0% and the water content is decreased accordingly.

The viscosity of this shampoo is extremely low, below 2 seconds.

EXAMPLE 12

Example 10 is repeated but the Arquad B-100 content is increased to 1.5% and the water content decreased accordingly.

This resultant shampoo has a viscosity of 2 seconds on No. 5 Raymond tube.

EXAMPLE 13

Example 10 is repeated but the Arquad B-100 ingredient is omitted and the water content is increased accordingly.

EXAMPLE 14

|  |  | % |
| --- | --- | --- |
| Lonzaine 12 C |  | 12.0 |
| Ammonyx MO |  | 4.5 |
| Merquat 100 | Part 2 | 0.1 |
| Perfume |  | 1.0 |
| Deionized Water |  | 75.4 |
| Polysorbate 20 |  | 3.0 |
| Climbazole | Part 1 | 2.0 |
| LMDEA |  | 2.0 |

Part 1 ingredients are combined and heated to 110° F. This mixture is cooled and added to part 2 ingredients with stirring. D & C Green No. 5 (0.02%) and Formalin (0.08%) are subsequently added. The resultant shampoo is a clear liquid of low viscosity.

EXAMPLE 15

|  | % |
| --- | --- |
| Lonzaine CS | 12.0 |
| Ammonyx MO | 4.5 |
| Merquat 100 | 0.1 |
| Fragrance | 1.0 |
| Polysorbate 20 | 3.0 |
| Climbazole | 2.0 |
| LMDEA | 2.0 |
| D & C Green No. 5 | 0.01 |
| Formalin | 0.08 |
| D. I. water | 75.31 |

This shampoo is prepared in accordance with the procedure of Example 14 and results in a clear liquid of low viscosity.

EXAMPLE 16

|  | % |
| --- | --- |
| Lonzaine C | 12.0 |
| Ammonyx MO | 4.0 |
| Arquad B-100 | 1.0 |
| Frangrance | 1.0 |
| Polysorbate 20 | 3.0 |
| LMDEA | 2.0 |
| Climbazole | 2.0 |
| D. I. water | 75.0 |

This formulation is clear and has a viscosity of 31.6 seconds.

EXAMPLE 17

|  | % |
| --- | --- |
| Lonzaine C | 12.0 |
| Ammonyx MO | 4.5 |
| Polysorbate 20 | 3.0 |
| LMDEA | 2.0 |
| Climbazole | 2.0 |
| Merquat 100 | 0.1 |
| Deionized Water | 76.4 |

This product is clear.

This same formula with 4.0 and 5.0% Climbazole results in a hazy liquid.

EXAMPLE 18

|  | % |
| --- | --- |
| Lonzaine C | 12.0 |
| Ammonyx MO | 4.5 |
| Polysorbate 20 | 3.0 |
| LMDEA | 2.0 |
| Climbazole | 5.0 |
| Arquad B-100 | 1.0 |

| | % |
|---|---|
| Deionized Water | 72.5 |

This product is a clear liquid. The substitution of Arquad for the Merquat permitted the use of higher concentrations of Climbazole.

EXAMPLE 19

| | % |
|---|---|
| Lonzaine C | 12.0 |
| Ammonyx MO | 4.5 |
| Polysorbate 20 | 3.0 |
| LMDEA | 2.0 |
| Climbazole | 7.5 |
| Arquad B-100 | 1.0 |
| Deionized Water | 70.0 |

This product is a hazy liquid. The concentration of Climbazole is too great for complete solubilization.

All of the aforedefined shampoo formulations except where otherwise indicated (such as for comparison purposes) are of useful viscosity, and possess good foaming properties, anti-microbial activity, cleaning efficacy and conditioning properties. Hair shampooed with these compositions feels exceptionally clean, is easy to comb and manageable.

Variations in the above formulations may be made. For example, other amine oxides may be substituted for the myristyl dimethyl amine oxide such as the lauryl dimethyl amine oxide, cetyl dimethyl amine oxide and the like. Similarly other betaines may be substituted for the cocobetaine such as cocoamidopropylbetaine, cocoamidopropylsulfobetaine and the like. The specified cationic quaternary polymer may be replaced by other water-soluble quaternary polymers.

Likewise, the amounts of each of the nonionic and amphoteric components as well as the cationic quaternary polymer may be varied within the designated percentages aforedefined without adversely affecting the solubility of the antidandruff agent.

The invention has been described with respect to various examples and embodiments but is not to be limited to these because it is evident that one of skill in the art with the present application before him will be able to utilize substituted and equivalents without departing from the spirit of the invention.

We claim:

1. A homogeneous liquid amphoteric-nonionic based antimicrobial conditioning shampoo containing about 0.5-2.5% of the water insoluble antimicrobial compound, 1-imidazolyl-1-(4-chlorophenoxy)-3,3-dimethyl-butan-2-one, solubilized in an aqueous vehicle comprising:
   a. about 6-30% by weight of a betaine, sulfobetaine, amidobetaine, amidosulfobetaine or combinations thereof,
   b. about 1-7.5% by weight of a dimethyl higher alkyl tertiary amine oxide,
   c. about 1-7% by weight of a higher fatty acid mono- or di-ethanolamide,
   d. about 0.1-5% by weight of a polyoxyethylene hexitan mono-higher fatty acid ester containing 10-80 moles ethylene oxide per mole, and
   e. about 65-80% water.

2. A shampoo in accordance with claim 1, wherein the polyoxyethylene hexitan monoester is polyoxyethylene sorbitan monolaurate containing 20 mol ethylene oxide per mol.

3. A shampoo in accordance with claim 2, wherein the amine oxide is myristyl dimethyl amine oxide.

4. A shampoo in accordance with claim 3, wherein the ethanolamide is lauric myristic diethanolamide.

5. A shampoo in accordance with claim 4, wherein the betaine is cocodimethyl betaine.

6. A shampoo in accordance with claim 1, wherein the aqueous vehicle contains about 0.01-0.1% by weight of a polymerized quaternized ammonium compound having the formula:

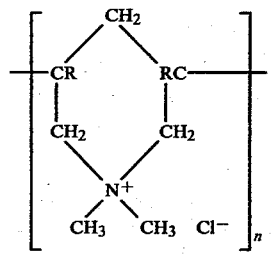

wherein R is a hydrogen or methyl and n is an integer in the range of 500 to 1,000.

7. A shampoo in accordance with claim 1, wherein the shampoo is a clear liquid.

8. A shampoo in accordance with claim 7, wherein the aqueous vehicle comprises about 7.5-15% by weight of an amphoteric agent selected from the group consisting of betaines, sulfobetaines, amidobetaines, amidosulfobetaines and mixtures thereof; about 1.0-2.5% by weight of a polyoxyethylene hexitan mono-higher fatty acid ester having 20 moles of ethylene per mol; about 3-5% by weight of dimethyl higher alkyl tertiary amine oxide and about 1-7% by weight of a higher fatty acid mono- or diethanolamide.

9. A method of simultaneously cleansing, and conditioning the hair in a single operation by shampooing with the liquid composition of claim 1.

* * * * *